United States Patent [19]
Richards

[11] Patent Number: 5,925,190
[45] Date of Patent: Jul. 20, 1999

[54] PRODUCTION OF FRUCTOSE DIANHYDRIDE PRODUCTS FROM INULIN

[75] Inventor: Geoffrey N. Richards, Missoula, Mont.

[73] Assignee: The University of Montana, Missoula, Mont.

[21] Appl. No.: 08/656,489

[22] Filed: May 31, 1996

Related U.S. Application Data

[63] Continuation-in-part of application No. 08/466,058, Jun. 6, 1995, abandoned.
[51] Int. Cl.$^6$ .......................... C08B 30/00; C13K 30/00; A23C 9/12; C12P 19/14
[52] U.S. Cl. .................................. 127/34; 127/29; 127/36; 127/42; 127/44; 426/61; 426/658; 435/99; 435/101; 435/105
[58] Field of Search .................................. 127/34, 29, 36, 127/42, 44; 426/61, 658; 435/99, 101, 105

[56] References Cited

U.S. PATENT DOCUMENTS

| | | | |
|---|---|---|---|
| 4,758,515 | 7/1988 | Barwald et al. | 435/99 |
| 4,871,574 | 10/1989 | Yamazaki et al. | 426/622 |
| 5,057,418 | 10/1991 | Uchiyama et al. | 435/99 |
| 5,206,355 | 4/1993 | Richards et al. | 536/4.1 |
| 5,318,794 | 6/1994 | Richards | 426/658 |

FOREIGN PATENT DOCUMENTS

| | | | |
|---|---|---|---|
| 05168419 | 7/1993 | Japan | A23K 1/16 |
| WO94/27617 | 12/1994 | WIPO | A61K 31/715 |
| WO94/27618 | 12/1994 | WIPO | A61K 31/715 |

OTHER PUBLICATIONS

Chemical Abstracts Publication –1994, 120:159111e month not available.
Ponder et al., "Pyrolysis of Inulin, Glucose and Fructose", Carbohydr. Res., 244 pp. 341–359 (1993). Dec. 1992.
Defaye et al., "Acetal and Ester Protecting–Groups in the Hydrogen Fluoride–Catalyssed Synthesis of D–Fructose and L–Sorbose Difuranose Dianhydrides", Carbohydr. Res., 174 pp. 323–329 (1988). Oct. 1987.
Defaye et al., "Selective protonic activation of isomeric glycosylfructoses with pyridinium poly(hydrogen fluoride) and synthesis of spirodioxanyl oligosaccharides", Carbohydr. Res., 273 pp. 223–247 May 1992.
Defay et al., "The Behavior of L–Sorbose Towards Anhydrous Hydrogen Fluoride", Carbohydr. Res., 152 pp. 89–98 (1986). Aug. 1985.
Defaye et al., "The Behavior of D–Fructose and Inulin Towards Anhydrous Hydrogen Fluoride", Carbohydr. Res., 136 pp. 53–65 (1985). May 1984.

*Primary Examiner*—Karl Group
*Assistant Examiner*—Patricia L. Hailey
*Attorney, Agent, or Firm*—McDermott, Will & Emery

[57] ABSTRACT

Inulins are pyrolyzed to di-D-fructose dianhydrides in good yield by heating at atmospheric pressure to a temperature sufficiently high to melt the inulin, or pyrolyzing in the presence of a hydroxy carboxylic acid such as citric acid, to melt temperatures of the mixture. The pyrolyzed inulins are used in foodstuffs to increase the relative proportions of bifido bacteria in the digestive tracts of humans and domesticated animals.

21 Claims, 3 Drawing Sheets

PRODUCTION OF FRUCTOSE DIANHYDRIDE PRODUCTS FROM INULIN

CROSS-REFERENCE TO RELATED APPLICATION

This application is a continuation-in-part of U.S. patent application Ser. No. 08/466,058, filed Jun. 6, 1995, now abandoned, the content of which is incorporated herein in its entirety by reference made thereto.

TECHNICAL FIELD

The present invention relates to a method of producing fructose dianhydrides from inulin, as well as trimers and higher oligomers formed by the sequential addition of glycosyl units to said dianhydrides, the products produced thereby, and compositions containing the products. In particular, the present invention relates to a method of producing difructose dianhydrides, related trimers and higher oligomers, in high yield from inulin and their use as bifidus factors.

BACKGROUND OF THE INVENTION

Fructose oligosaccharides have nutritional advantages in animal and human diets. These oligosaccharides modify the relative proportions of intestinal bacteria and in particular are effective in increasing the proportion of bifido bacteria in the digestive tract of animals. Thus, products containing a high percentage of fructose oligosaccharides such as difructose dianhydrides, and higher oligomers derived therefrom, are in demand as nutritional additives.

In addition to disease and stress, the control of microflora is important in humans and especially animals. Microflora comprise bacteria found predominantly on the skin of animals and in the intestinal tracts. It is commonly believed that certain components of the normal intestinal microflora influence health and control of disease. The presence of microflora influences the point at which meat, milk and eggs will begin to spoil. Moreover, a large bacterial count is responsible for premature food spoiling.

Efforts to control disease caused by pathogenic microflora are expensive and sometimes ineffective, and add to the cost of producing meat, egg and milk products. Further, the administration of expensive antibiotics also adds to the costs of raising livestock. These costs are typically absorbed by the consumer.

Caramels are confectionery products obtained by heating reducing sugars such as glucose and sucrose. The time generally required to achieve caramelization is several hours, typically from 3 to 9 hours. The composition of caramels has been studied previously and caramels prepared from sucrose have been shown to contain small amounts of oligosaccharides, predominantly glucose disaccharides.

U.S. Pat. No. 5,318,794 and published PCT Applications WO94/27617 and WO94/27618 of the Applicant, disclose the production of caramels, e.g. sucrose oligosaccharides (STO), useful as bifidus factors, by pyrolysis of sucrose in the presence of small amounts of an organic acid such as citric acid. U.S. Pat. No. 5,206,355 discloses the heating of sucrose in a melt in the presence of an organic acid, e.g. citric acid, to form various trisaccharides and polymers.

Japanese Published Patent Applications JP 05168419 and AZ 930702 disclose difructose dianhydrides (DFDA) made by enzymic treatment of inulin, added to chicken feed (0.25 to 0.5%) to increase growth rates about 5–12% and decrease lipids 6–10% (Chem. Abs. 1994, 119, 159111).

Ponder et al. "Pyrolysis of Inulin, Glucose and Fructose", Carbohydrate Research, 244 (1993) 341–359, describes the pyrolysis of inulin. In Ponder et al., inulin was vacuum pyrolyzed for one hour at 240° C. and treated with various basic additives such as sodium chloride, sodium hydroxide and calcium hydroxide. As reported on page 354 of that publication, difructose dianhydrides (DFDA's) were produced during the vacuum pyrolysis of inulin. However, the combined yields reported were very low.

The present invention provides a method for the pyrolysis of inulin to produce difructose dianhydrides, as well as trimers and higher oligomers thereof, in substantially greater yield than known previously. Further, the dianhydrides produced from the pyrolysis of inulin according to the invention have substantial nutritional advantages as bifidus factors.

SUMMARY OF THE INVENTION

It is accordingly one object of the present invention to provide a method for the production of difructose dianhydrides, as well as trimers and higher oligomers thereof formed by the sequential addition of glycosyl moieties thereto.

A further object of the invention is to provide a novel method for the pyrolysis of inulin to produce difructose dianhydrides, trimers and higher oligomers, in substantial yield and purity.

An even further object of the invention is to provide substantially pure difructose dianhydrides, trimers and higher oligomers thereof, by pyrolysis of inulin in the presence of an organic carboxylic acid.

Other objects and advantages of the present invention will become apparent as the description thereof proceeds.

In satisfaction of the foregoing objects and advantages, the present invention provides a method for the production of difructose dianhydrides, trimers and higher oligomers thereof, which comprises pyrolyzing inulin, optionally in the presence of a food grade acid, and under atmospheric conditions.

The present invention also provides novel difructose dianhydrides and higher oligomers in substantial purity produced by the pyrolysis of inulin in the presence of an hydroxy carboxylic acid, and use of the difructose dianhydrides and higher oligomers as bifidus factors.

BRIEF DESCRIPTION OF THE DRAWINGS

Reference is now made to the drawings accompanying the application.

DESCRIPTION OF THE INVENTION

Figure 1:
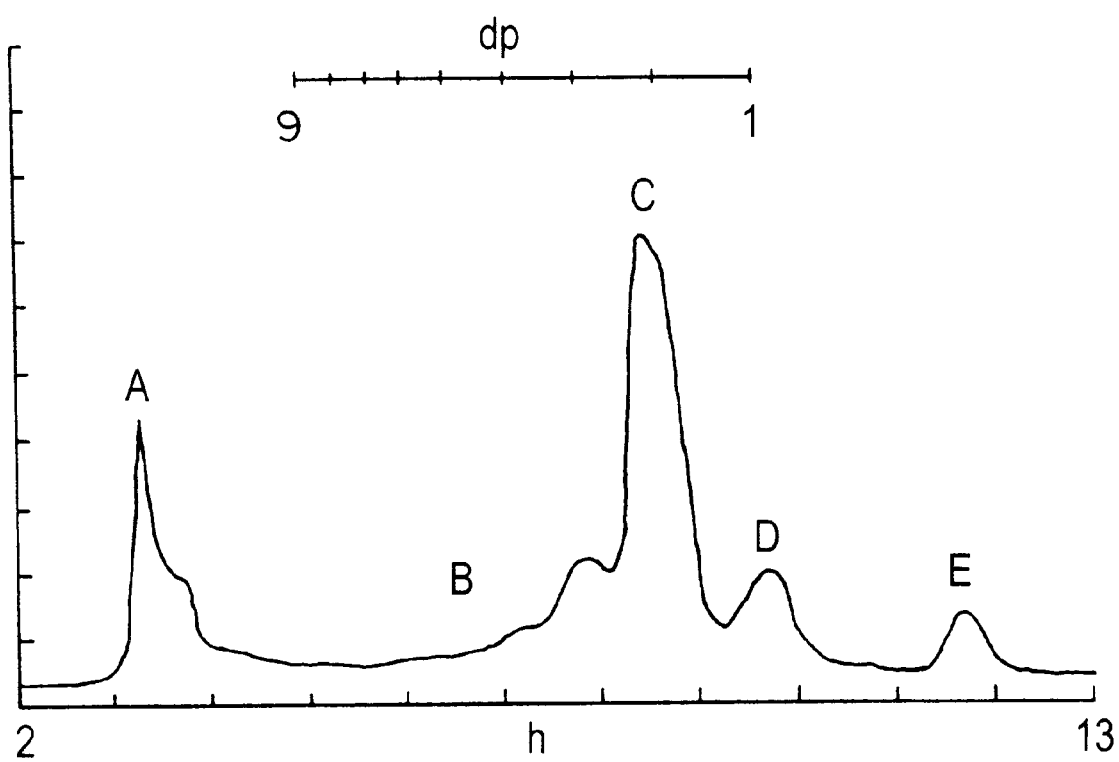
FIG. 1 depicts a gel permeation chromatography fractionation profile of the inulin pyrolysis of the invention as described in Example 4.

According to the present invention, it has been unexpectedly found that it is possible to greatly increase animal growth rates and health by administering a product produced by pyrolysis of inulin having a high content of, in particular, difructose dianhydrides. The animal husbandry method and composition according to the present invention enhances the growth rate and health of any animal, and particularly, animals which are kept as livestock to supply meat, milk or eggs. The present invention is also applicable for use on other domestic animals including horses, cats, dogs, rabbits, etc., as well as fish. In the livestock industry, feed constitutes the major cost of producing consumer products including meat, milk or eggs. The present invention represents a significant achievement in reducing the costs associated with the livestock industry, while at the same time improving animal health.

In addition, the compositions of the present invention are useful for human consumption and, in particular, as an additive in infant formula and baby food. By altering the relative proportions of microflora in a human, the compositions of the present invention provide a useful health additive for the treatment of intestinal disorders, in particular diarrhea.

Inulin is a fructose polymer (β-1,2-D-fructofuran, with a sucrose end group), which is a plant food reserve especially abundant in chicory root, Jerusalem artichokes and dahlias. Sucrose is the disaccharide α-D-glucopyranosyl-β-D-fructofuranoside, obtained primarily from sugar cane and sugar beet.

According to this invention, inulin is pyrolyzed under specially defined conditions to produce substantial yields of difructose dianhydrides of high purity, as well as trimers and higher oligomers thereof. The difructose dianhydrides (DFDA's) of the present invention are di-D-fructose dianhydrides of several types.

One of the major components was identified as α-D-fructofuranose-β-D-fructofuranose-1,2':2,3'-dianhydride (di-D-fructose anhydride III), of the following formula (referred to herein as compound 4):

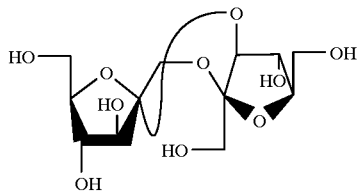

A second major dianhydride is β-D-fructofuranose-β-D-fructofuranose-1,2':2,3'-dianhydride of the following formula (referred to herein as compound 7):

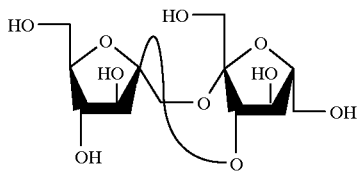

A third dianhydride is α-D-fructopyranose-β-D-fructopyranose-1,2':2,1'-dianhydride of the following formula (referred to herein as compound 8):

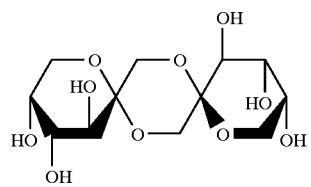

A fourth dianhydride is β-D-fructofuranose-α-D-fructopyranose-1,2':2,1'-dianhydride of the following formula (referred to herein as compound 9):

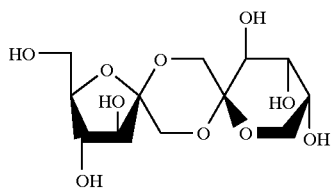

A fifth dianhydride is di-α-D-fructofuranose-1,2':2,1'-dianhydride of the following formula (referred to herein as compound 10):

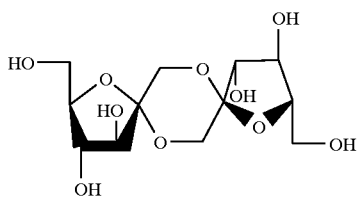

A sixth dihydride is α-D-fructofuranose-α-D-glucopyranose 1,1':2,2'-dianhydride of the formula (referred to herein as compound 11):

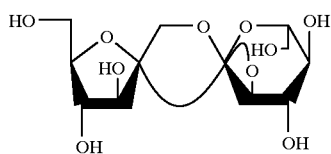

A seventh dianhydride is α-D-fructofuranose-β-D-fructopyranose 1,2':2,1'-dianhydride of the formula (referred to herein as compound 12):

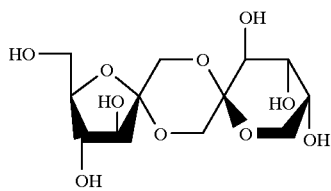

An eighth major dianhydride is α-D-fructofuranose-β-D-fructofuranose-1,2':2,1'-dianhydride of the formula (referred to herein as compound 13):

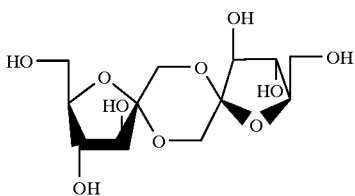

A ninth dianhydride is α-D-fructofuranose-α-D-fructopyranose-1,2':2,1'-dianhydride of the formula (referred to herein as compound 14):

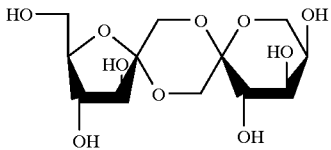

A tenth dianhydride is di-β-D-fructofuranose-1,2':2,1'-dianhydride of the formula (referred to herein as compound 15):

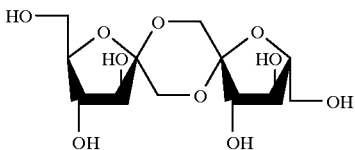

An eleventh dianhydride is β-D-fructofuranose-β-D-fructopyranose-1,2':2,1'-dianhydride of the formula (referred to herein as compound 16):

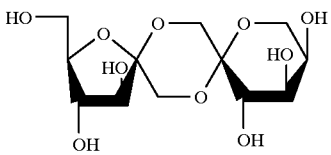

An additional dianhydride was not isolated but was identified as a dianhydride by mass spectrometry of the per-O-trimethylsilyl ether.

Other isomeric DFDA's may also present in the pyrolysis mixture. As discussed below, trimers and higher oligosaccharides including those produced by the sequential addition of glucosyl moieties of the dianhydrides are also present.

According to the present invention, inulin is pyrolyzed to difructose dianhydrides and their derivatives for use as bifidus factors. The pyrolysis is preferably carried out at atmospheric pressure, either with or without a hydroxy carboxylic acid as a co-reactant. The pyrolysis is carried out by heating the inulin under atmospheric conditions at temperatures sufficiently high (e.g., from about 150° C. to about 205° C.) to cause the inulin to form a melt in which pyrolysis takes place. In one preferred procedure, pure inulin is heated to pyrolysis in the absence of a co-reactant such as an anhydrous organic carboxylic acid. The inulin is heated to melting in the range of about 200–205° C. to form a melt, as no pyrolysis takes place until the inulin powder forms the melt. Pyrolysis occurs in 1 to 10 minutes.

In this method of the invention, the inulin is preferably heated under atmospheric conditions with agitation in an open container at a temperature in the range of about 200–205° C. The inulin will form a white paste or dough which then darkens and softens to become a pale brown fluid as the powder melts. Considerable foaming and darkening may be noted. After a few minutes (e.g., 5 to 30 minutes), the sample is removed as a cooled melt. From this dry product, the fructose dianhydrides, trimers and higher oligomers may be recovered.

In a further preferred embodiment, a hydroxy carboxylic acid, preferably anhydrous, is used as a co-reactant. It is preferred to incorporate about 0.5–3.0% of a hydroxy carboxylic acid with the inulin for the pyrolysis reaction. The organic acid is preferably a non-volatile food grade acid such as citric acid, tartaric acid, malic acid, and the like or mixtures thereof. Anhydrous citric acid is highly preferred for use in the reaction.

The inulin-acid mixture is preferably prepared by pulverizing a mixture of the inulin and organic acid in dry form to produce an intimate powder mixture. It has been discovered that the yield of the DFDA's is substantially increased to the range of above about 40% in the final caramel product by use of the organic acid as a co-reactant. In addition, the optimized product, an inulin thermal oligosaccharide caramel (ITOC), is an advantageous product over sucrose thermal oligosaccharide caramels (STOC), because almost all of the material in the inulin oligosaccharide caramel (with the exception of about 15% monosaccharides) appears to be active as a bifidus factor, whereas in the STOC, about half the product is inert in this respect. The trimers and higher oligosaccharides contained in the product are also bifidus factors. By trimers and higher oligosaccharides (oligomers) it is meant that such compounds contain three or more sugar groups.

Accordingly, the product produced by pyrolysis of inulin in combination with a co-reactant such as an anhydrous hydroxy carboxylic acid, is a highly preferred embodiment of the present invention.

The mixture of inulin and organic acid such as citric acid, is stirred while heating to temperature. The addition of the hydroxy carboxylic acid lowers the melting point of the inulin from an original melt temperature of about 205° C. where pyrolysis is very rapid and difficult to control to about 150° C. where the reaction melt is easy to stir and there is a controllable reaction time. For example, by heating the mixture at a temperature of about 150° C. to 205° C., the pyrolysis of the melt can be carried out in a period of about 1 minute to 1 hour, preferably in about 30 minutes or less.

After completion of the pyrolysis reaction, the cooled product is an amber colored glassy material. The product appears to be a complex mixture of DFDAs containing other types of disaccharides, but with DFDAS totalling about 36% of the caramel product. The presence of a complex of trisaccharides and higher oligosaccharides is also noted and such compounds are also bifidus factors and a further embodiment of the invention.

It is a feature of the invention that difructose dianhydrides are obtained from pure inulin in yields of at least 26% and when the pyrolysis is conducted in the presence of an hydroxy carboxylic acid such as citric acid, yields are obtained on the order of 36–40%, thus representing a substantial advance in this art.

The inulin pyrolyzed products of the invention and the difructose dianhydrides, as well as the trimers and higher oligomers contained therein, modify the relative types of intestinal microflora, and are effective in increasing the proportion of bifido bacteria and lactobacilli in the digestive tract of animals including poultry, swine, cattle, etc. In addition, it has been discovered that the products of the invention may be administered to livestock and other animals to increase animal growth and improve animal health.

According to the present invention, the inulin-pyrolyzed products are administered in the feed stock for convenience, but any other method of administration may be used. The products can be dissolved in the animal water supply or encapsulated in a sustained release system which is administered orally to the animal. Any other administration means may be used. However, it should be appreciated that oral administration is preferred in order to modify the specific microflora in the gastrointestinal tract of the animal so as to enhance the health of the animal.

The methods of the present invention provide particular advantages in improving poultry feed. Thus, using the methods of the invention, marketing time for broiler chickens, for example, can be reduced. Further, improved feed conversions can be expected. Also, advantages are achieved in improving breast weight and dressed carcass weight ratios.

Further, and in accordance with the present invention, livestock or animals to which the products of the invention are administered exhibit changes in microflora within the gastrointestinal tract of the animal. Thus, the compositions according to the present invention further comprise a method of altering the relative percentage of specific microflora within the gastrointestinal tract of an animal to enhance the health of the animal.

Among the microflora known to exist in the gastrointestinal tract of animals, bifido bacteria and lactobacilli are considered to be beneficial intestinal bacteria, while others such as *E. coli* and *salmonella* are detrimental to animals in terms of both health and nutrition.

It has been discovered according to the present invention that animals fed a diet incorporating pyrolyzed inulins exhibit increased numbers of bifido bacteria and lactobacilli. An increase in these microflora, as is known, reflects the fact that the bifido bacteria and lactobacilli utilize the fructose oligosaccharides, while most detrimental microflora do not.

Thus, in accordance with these and other objectives, the present invention is useful not only for greatly increasing the growth rate of animals, but is also useful for altering the specific microflora within the gastrointestinal tracts of animals and reducing the possibility of carcass contamination by pathogenic microorganisms.

While it is preferred that the pyrolyzed inulin be administered in the feed stock of the animal for convenience, any other method of administration may be used. Accordingly, the present invention also relates to a method of preparing an improved animal feed stock and the prepared animal feed stock produced thereby. The pyrolyzed inulin is preferably mixed with an animal feed stock in amount of from about 0.05 to about 7.5 wt. % and more preferably from about 0.5 to about 4.0 wt. %.

As an example of a method of preparing the improved animal feed stock, preferably the pyrolyzed inulin, sucrose, DFDA's, trimers or higher oligomers are mixed within animal feed stock by the process of dissolving in water, neutralizing the acid if any, mixing the solution with feed in the desired amount, and thoroughly drying the feed. The acid present is typically citric acid, and this is preferably neutralized with sodium carbonate. However, it is understood that any other neutralization agent may be used as long as the agent is non-toxic and not otherwise harmful to animals. The feed may be dried, e.g., at about 55° C.

Feed stock for poultry or other animals raised for meat consumption typically comprises at least one of the following including all of the cereal grains such as corn, wheat and wheat by-products. Poultry feed generally includes a protein supplement, the protein being derived from any of the following including fish meal, meat scrap, tankage, dairy by-products, peanut meal, soybean meal, etc.

As a further example, young calves fed milk or milk replacer may have the pyrolyzed inulin, sucrose, DFDAS, trimers or higher oligomers, or mixtures thereof, added to their diet to prevent or cure diarrhea and to improve production.

As an additional example, sheep and horses require barley, oats and wheat. The pyrolyzed inulin, sucrose, DFDAs, trimers or higher oligomers may be administered with oats, barley and wheat in the form of a mash or other composition.

If desired, the pyrolyzed inulin, sucrose, DFDA, trimers or higher oligosaccharides may be initially mixed with one or more excipients selected from the group consisting of antibiotics, vitamins, flavorings and colorings, or any other additive which is desired. Alternatively, such excipients may be added to the feed after the addition of pyrolyzed material.

The following examples are presented to illustrate the invention, and should not be construed as a limitation thereto.

EXAMPLE 1

Inulin (40 g) from Dahlia tubers was passed through a 200 Tyler mesh sieve and intimately mixed with 200 mesh anhydrous, amorphous citric acid (0.6 g) by tumbling for 30 minutes. A 10 g sample of the mixed powders was stirred by a contoured stirrer in a round bottomed flask while heating in an oil bath at 150±1° C. The powder melted to a mobile liquid in about 8 minutes and was stirred at the same temperature for a further 20 minutes. The cooled product was an amber-colored glass. Analysis of a sample by TMS-GC (tri-O-methylsilylation-gas chromatography), using the averaged results from five pure DFDA's to determine response factors to glucitol standard, showed the presence of a complex mixture of DFDA's and possibly other types of disaccharides, totalling 36% of the caramel. A complex of trisaccharides was also observed and their presence, plus higher oligosaccharides, was confirmed by gel permeation chromatography (GPC) on Biogel P2.

EXAMPLE 2

The same powder mixture was heated and stirred at 160° C. for about 7 minutes after melting. The caramel contained 38% DFDA's plus tri- and higher-oligosaccharides.

EXAMPLE 3

The procedure of example 1 was repeated with stirring and heating at 150° C. for about 14 minutes after melting. The caramel contained 40% DFDA's plus tri- and higher-oligosaccharides.

EXAMPLE 4

Inulin was pyrolyzed in an open test tube with stirring at 200° C. for about 7 minutes in an oil bath. The highly-colored residual product from this pyrolysis was fractionated by GPC, as shown in FIG. 1. A continuum of polymers and oligomers, A and B, was observed in the GPC trace; these could be fragments of inulin or the products of thermal recombination. The majority of the color was in the region A which comprises material excluded by the gel. Those portions of the peaks C-E which were amenable to chromatography were identified by liquid chromatography (LC) and gas chromatography-mass spectrometry (GC-MS) of the per-O-trimethylsilyl derivatives. C contained di-D-fructose dianhydrides and a trace of 2,6-anhydro fructofuranose, D contained glucose and fructose in similar amounts. E was shown to be 5-hydroxymethyl-2-furaldehyde.

GC-MS of the per-O-trimethylsilylated pyrolysis product revealed a cluster of five major and several minor peaks whose retention times and mass spectra were consistent with di-D-fructofuranose dianhydrides (~26% based on inulin). These constituted a major part of the products amenable to GC; 2,6-anhydro-D-fructofuranose (~1%), glucose (~4%) and significant fructose (~30%) were also present. A cluster of trisaccharides (~15%) was again observed. A fraction containing predominantly trisaccharides with some disaccharides was subsequently isolated by GPC. Mild hydrolysis of this fraction followed by reduction and per-O-trimethylsilylation of the products revealed, by gas chromatography/flame ionization detection (GC-FID) and GC-MS, the presence of fructose and di-D-fructose dianhydrides (trimer) in the ratio 1:1.4. The profile of di-D-fructose dianhydrides thus obtained was almost identical with that found in fraction C. This indicates that oligosaccharides were forming either by addition of fructosyl residues to already formed di-D-fructose dianhydrides or by cleavage of a di-D-fructose dianhydride plus a fructosyl residue or residues from a polymer chain as discussed below.

Three components, compounds 4, 7 and 13, made up ~75% of the dianhydrides. These were isolated by preparative LC using successive applications of two different column-solvent systems and were identified as the compounds 4, 7 and 13 mentioned above.

The relative abundances of di-D-fructose dianhydride products have been explained by other authors in terms of differing reaction conditions permitting more or less equilibration to occur. See Defaye et al, *Carbohydr. Res.*, 174 (1988) 323–329; *Carbohydr. Res.*, 136 (1985) 53–65; *Carbohydr. Res.*, 152 (1986) 89–98; and *Carbohydr. Res.*, 237 (1992) 223–247. A survey was made of the ratio of di-D-fructose dianhydrides obtained by the pyrolysis of inulin in this invention. A, B and D correspond respectively to compounds 4, 7 and 13; C and E, although they were not isolated, have mass spectra consistent with di-D-fructofuranose dianhydrides. The relative abundances of di-D-fructose dianhydride products A–E from inulin pyrolysis, as determined by TMS-GC were as follows: A=1.0; B=0.58; C=0.27; D=1.0; and E=0.25, quantified as per-O-Me$_3$Si derivatives.

These results are quite different from the mixture of products obtained by the treatment of inulin with anhydrous HF by Defaye et al., supra, *Carbohydr. Res.* 136 (1985) 53–65, in which the di-D-fructose dianhydride products contained either two or one fructopyranose rings and no difuranose products were observed. Additionally, the major products include compounds 4 and 13, which are not considered to be the most thermodynamically stable of the difuranose dianhydrides. This seems to indicate that an equilibrium position has not been attained.

EXAMPLE 5

Figure 2A:
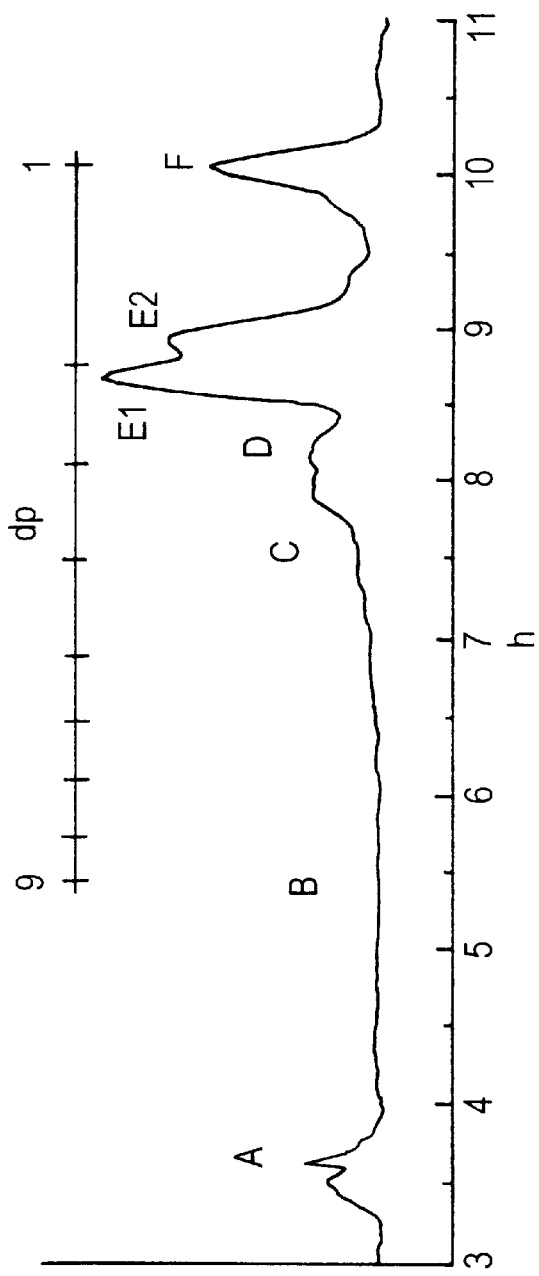
FIGS. 2(a) and 2(b) depict the results of gel permeation chromatography of inulin (a) and sucrose (b) caramels on Bio-Gel P2 as described in Example 5.
Figure 2B:
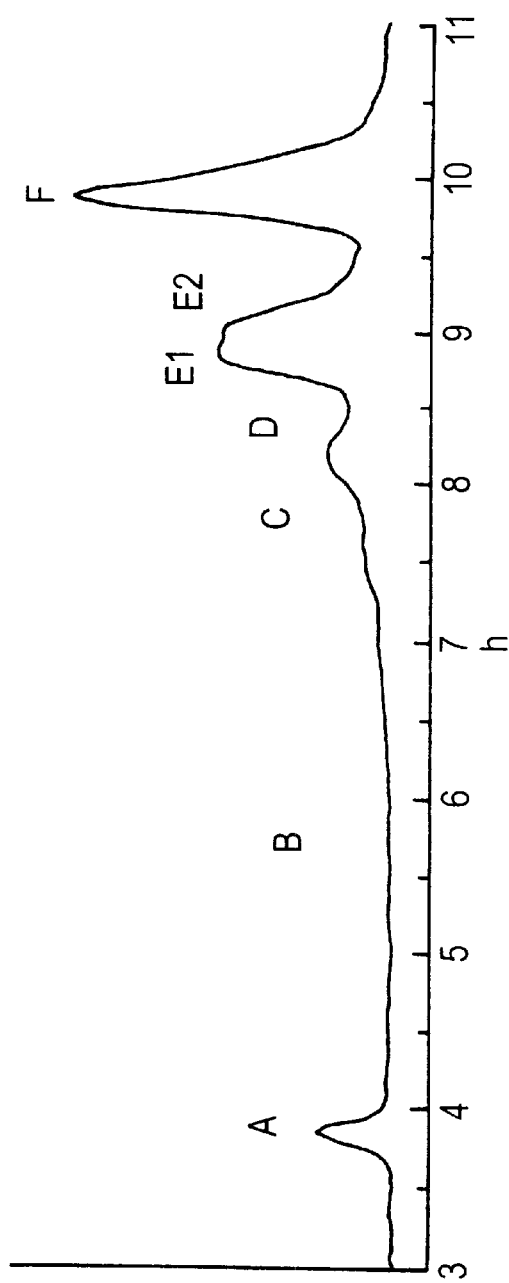

Caramels formed by the thermal treatment of anhydrous acidified sucrose and of inulin were analyzed by size exclusion chromatography, the elution profile of which is depicted in FIG. 2. In the case of inulin, polymeric material was excluded from the column. Fraction A contained citric acid. Fraction B contained pentamers and yet higher oligomers, whereas Fraction C contained tetramers and Fraction D contained trimers. Fractions E1 and E2 contained dimers, which in the case of inulin were predominantly di-D-fructose dianhydrides. In the case of sucrose, on the other hand, these fractions contained significant amounts of singly-linked disaccharides along with the dianhydrides. Fraction F contained glucose and fructose, with glucose predominating in the case of the sucrose source.

Figure 3:
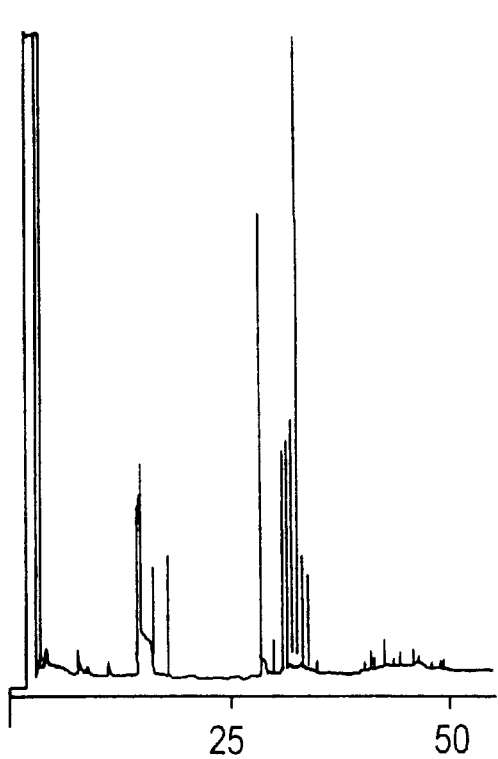
FIGS. 3(a) and 3(b) depict the results of GC-FID of the per-O-trimethylsilyl ethers of inulin (a) and sucrose (b) caramels as described in Example 5.
Figure 3:
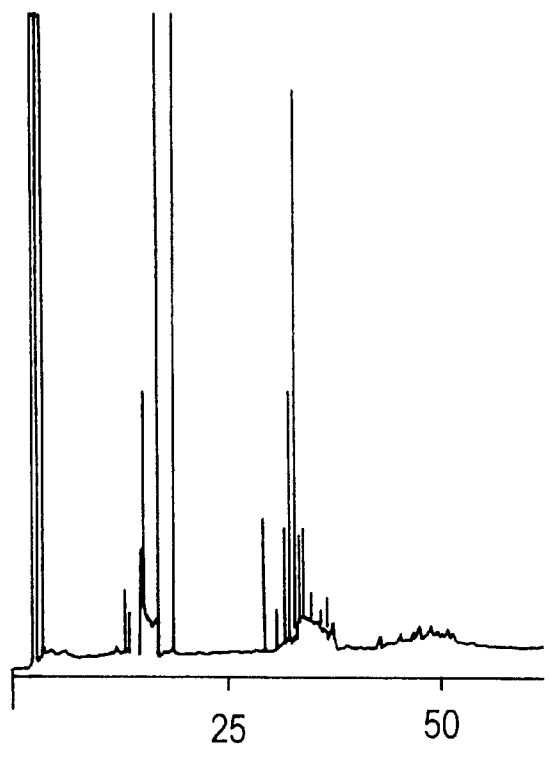

In the dimer fraction for inulin, GC-FID traces of the per-O-Me$_3$Si derivatives revealed twelve peaks corresponding to di-D-fructose dianhydrides (FIG. 3). For sucrose, a thirteenth peak was also observed as well as single-linked disaccharides. The following dianhydrides were identified in both the inulin and sucrose pyrolysis product: α-D-fructofuranose-β-D-fructfuranose-1,2':2,3'-dianhydride (compound 4); di-β-D-fructofuranose-1,2':2,3'-dianhyride (compound 7); α-D-fructopyranose-β-D-fructopyranose-1, 2':2,1'-dianhydride (compound 8); β-D-fructofuranose-α-D-fructopyranose-1,2':2,1'-dianhydride (compound 9); di-α-D-fructofuranose-1,2':2,1'-dianhydride (compound 10); α-D-fructofuranose-α-D-glucopyranose 1,1':2,2'-dianhydride (compound 11; found only in sucrose source sample); α-D-fructofuranose-β-D-fructopyranose 1,2':2,1'-dianhydride (compound 12); α-D-fructofuranose-β-D-fructofuranose-1, 2':2,1'-dyanhydride (compound 13); α-D-fructofuranose-α-D-fructopyranose-1,2':2,1'-dianhydride (compound 14); di-β-D-fructofuranose-1,2':2,1'-dianhydride (compound 15); and, β-D-fructofuranose-β-D-fructopyranose-1,2':2,1'-dianhydride (compound 16).

Compounds 4, 7, 12 and 13 have been previously isolated, as noted above. Compound 9 has also been previously described. The remaining compounds were identified by methylation analysis and NMR spectroscopy. Of these, compound 16 was found to have an identical $^{13}$C NMR with a previously published spectrum. Three other compounds (5, 6 and 17) are presumed dianhydrides because of the details of their mass spectra.

The trimer fraction (Fraction D above) from sucrose yielded dianhydrides, fructose and glucose, upon mild hydrolysis suggesting that this fraction contains a significant proportion of dianhydrides that have reacted during the pyrolysis reaction. The GC profile of the per-O-trimethylsilyl ethers reveals at least 26 peaks, indicating a great variety of trimer structures present in the caramel, with no single trimer being predominant. Structural analysis of compound 18 indicated that it is the 6,6'-di-O-glucopyranosyl derivative of compound 13. The $^{13}$C NMR spectrum of compound 19 was consistent with an assignment of α-D-fructofuranose-β-D-fructofuranose-1,2':2,1'-dianhydride (compound 13) substituted at O-6' of the β-D-fructofuranose residue. The substitution was determined by NMR to be an α-linked glucopyranosyl residue. Trisaccharide compound 20 was found to be compound 13 substituted at O-6' with a β-D-fructopyranose residue. It is likely that each of the trimers were derivatives of compound 13 because that compound is the dominant dianhydride present in the caramel.

Thus, a trisaccharide compound under the invention is 6,6'-di-O-glucopyranosyl-α-D-fructofuranose-β-D-fructofuranose-1,2':2,1'-dianhydride (referred to herein as compound 18) of the formula:

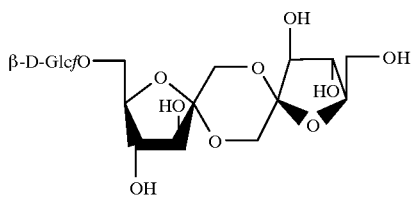

where β-D-GlcfO is a β-D-glucofuranosyl moiety.

A second trisaccharide compound under the invention is 6'-O-α-D-glucopyranosyl-α-D-fructofuranose-β-D-fructofuranose-1,2':2,1'-dianhydride (referred to herein as compound 19) of the formula:

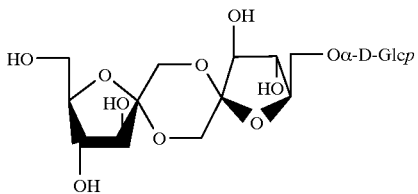

where O α-D-Glcp is an α-D-glucopyranosyl moiety.

A third trisaccharide compound under the invention is 6'-O-β-D-fructopyranosyl-α-D-fructofuranose-β-D-fructofuranose-1,2':2,1'-dianhydride (referred to herein as compound 20) of the formula:

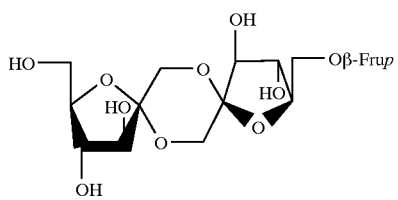

where O-β-Frup is a β-D-fructopyranosyl moiety.

Each of the above trisaccharides are useful as nutritional additive.

The invention has been described herein with reference to certain preferred embodiments; however, as obvious variations thereon will become apparent to those skilled in the art, the invention is to not to be considered as limited thereto.

We claim:

1. A method for the production of difructose dianhydrides, and trimers and higher oligomers thereof, which comprises pyrolyzing inulin under anhydrous conditions at atmospheric pressure and a temperature in the range of about 150° C. to 205° C. for a sufficient time to form one or more difructose dianhydrides, trimers or higher oligomers.

2. A method according to claim 1, wherein the inulin is heated at a temperature in the range of about 200° C. to 205° C. for a sufficient time to pyrolyze in a melt.

3. A method according to claim 2, wherein heating of the inulin is continued for from about 5 to about 30 minutes, the resulting melt product is cooled, and a dry product containing one or more fructose dianhydrides, trimers or higher oligomers thereof, is recovered.

4. A method according to claim 1, which comprises heating inulin in the presence of a food grade acid.

5. A method according to claim 4, wherein the food grade is an anhydrous hydroxy carboxylic acid.

6. A method according to claim 5 wherein heating of the inulin in the presence of the anhydrous hydroxy carboxylic acid is conducted at a temperature in the range of about 150° C. to about 200° C. for a period of about 1 minute to about 1 hour.

7. A method according to claim 6, wherein heating of the inulin in the presence of the anhydrous hydroxy carboxylic acid is conducted at a temperature in the range of 150° C. to 180° C. for about 1 minute to about 1 hour.

8. A method according to claim 5, wherein the anhydrous hydroxy carboxylic acid is a non-volatile food grade acid selected from the group consisting of citric acid, tartaric acid, malic acid, and mixtures thereof.

9. A method according to claim 4 wherein the food grade acid is present in an amount of about 0.1 to about 3% by weight based on the amount of inulin.

10. A method according to claim 4, wherein the inulin and food grade acid are mixed as dry powders prior to pyrolysis.

11. A pyrolyzed inulin produced by the process of claim 1.

12. A human or animal foodstuff mixture comprising a dietary food and a sufficient amount of a pyrolyzed inulin of claim 11 to increase bifido bacteria in the digestive tract of said animal.

13. An animal foodstuff according to claim 12, wherein the animal is a human or domesticated animal.

14. A method for increasing the proportion of bifido bacteria in the digestive tract of humans or domesticated animals which comprises administration thereto of a pyrolyzed inulin mixture of claim 12.

15. A pyrolyxed inulin containing difructose-D-dianhydride, trimers and higher oligosaccharides thereof, produced by the process of claim 1.

16. A pyrolyzed inuiln according to claim 15 wherein the difructose dianhydrides comprise one or more members selected from the group consisting of α-D-fructofuranose-β-D-fructofuranose-1,2':2,3'-dianhydride; β-D-fructofuranose-β-D-fructofuranose-1,2':2,3'-dianhydride; and α-D-fructofuranose-β-D-furctofuranose-1,2':2,1'-dianhydride; α-D-fructopytanose-β-D-fructopyranose-1,2':2,1'-dianhydride; di-α-D-fructofuranose-1,2':2,1'-dianhydride; α-D-fructofuranose-α-D-fructopyranose-1,2':2,1'-dianhydride; β-D-fructofuranose-β-D-fructopyranose-1,2':2,1'-dianhydride; 6,6'-di-O-glucopyranosyl-α-D-fructofuranose-β-D-fructofuranose-1,2':2,1'-dianhydride; 6'-O-β-D-glucopyranosyl-α-D-fructofuranose-β-D-fructofuranose-1,2':2,1'-dianhydride; and 6'-O-β-D-fructopyransyl-α-D-fructofuranose-β-D-fructofuranose-1,2':2,1'-dianhydride.

17. A pyrolyzed inuline according to claim 15 wherein the fructose dianhydrides and higher oligosaccharides total at least 20 weight percent of the pyrolyzed inulin product.

18. A method for the pyrolysis of inulin to produce difructose dianhydrides, and trimers and higher oligomers thereof, which comprises heating inulin at atmospheric pressure under anhydrous conditions and at a temperature in the range of about 200° C. to about 205° C. for a time period of about 5 minutes to about 30 minutes to produce an inulin pyrolysis product containing difructose dianhydrides, trimers and higher oligomers.

19. A method according to claim 18 wherein the hydroxy carboxylic acid is citric acid.

20. A method for the production of difructose dianhydrides, and trimers and higher oligomers thereof, which comprises mixing inulin with about 0.5 to 3 weight percent of a substantially non-volatile food grade organic carboxylic acid, and heating said mixture under anhydrous conditions to a temperature in the range of about 150° C. to about 200° C. for a period of about 1 minute to about 1 hour to produce a pyrolized inulin product containing mixtures of difructose dianhydrides and higher oligosaccharides in amounts of at least 20% by weight.

21. A method according to claim 20 wherein the organic carboxylic acid is selected from the group consisting of citric acid, malic acid, tartaric acid and mixtures thereof.

* * * * *